(12) United States Patent
Zamanzadeh et al.

(10) Patent No.: US 12,399,149 B2
(45) Date of Patent: Aug. 26, 2025

(54) ELECTROCHEMICAL PLANT ACTIVITY MONITOR

(71) Applicant: AGRIGENICS INC., Preston, PA (US)

(72) Inventors: Mehrooz Zamanzadeh, Pittsburgh, PA (US); Carolyn Tome, Pittsburgh, PA (US)

(73) Assignee: Agrigenics Inc., Presto, PA (US)

( * ) Notice: Subject to any disclaimer, the term of this patent is extended or adjusted under 35 U.S.C. 154(b) by 0 days.

(21) Appl. No.: 18/663,138

(22) Filed: May 14, 2024

(65) Prior Publication Data

US 2024/0295526 A1 Sep. 5, 2024

Related U.S. Application Data

(63) Continuation-in-part of application No. 18/072,011, filed on Nov. 30, 2022, which is a
(Continued)

(51) Int. Cl.
G01N 27/416 (2006.01)
G01N 27/30 (2006.01)
G01N 33/00 (2006.01)

(52) U.S. Cl.
CPC ......... *G01N 27/4168* (2013.01); *G01N 27/30* (2013.01); *G01N 33/0098* (2013.01)

(58) Field of Classification Search
CPC . A01G 7/00; A01G 7/04; G01N 27/27; G01N 27/30; G01N 27/327;
(Continued)

(56) References Cited

U.S. PATENT DOCUMENTS

| 4,039,942 A | 8/1977 | Glaser |
| 5,033,397 A | 7/1991 | Colburn |

(Continued)

FOREIGN PATENT DOCUMENTS

| JP | 2005-073680 | 3/2005 |
| JP | 2009-000093 | 1/2009 |

(Continued)

OTHER PUBLICATIONS

Dimkpa C., et al., "Methods for Rapid Testing of Plant and Soil Nutrients," Sustainable Agriculture Reviews, 2017, pp. 1-41. Retrieved from the Internet: URL: https://www.researchgate.net/profile/Christian-Dimkpa/publication/318423496_Methods_for_Rapid_Testing_of_Plant_and_Soil_Nutrients/links/5cf6d1b0a6fdcc847506349e/Methods-for-Rapid-Testing-of-Plant-and-Soil-Nutrients.pdf.

(Continued)

*Primary Examiner* — Peter M Poon
*Assistant Examiner* — Danielle A Clerkley
(74) *Attorney, Agent, or Firm* — Bauer and Joseph; Thomas Joseph

(57) ABSTRACT

A working electrode is inserted into the plant to monitor the health of the plant components or to detect physical, mechanical damage or environmental change in the soil or atmosphere. A standard electrode is inserted into soil surrounding the plant or in the plant itself. A data logger connects the working electrode and the standard electrode. The data logger measures the potential difference between the working electrode and the electrolyte to provide the ability to compare a measured potential difference with a predetermined critical potential difference for the plant. A second electrochemical cell can inject electrons and ions into the plant. The plant can be used as a sensor to monitor the environmental change in the soil or in the atmosphere.

20 Claims, 11 Drawing Sheets

Related U.S. Application Data continuation-in-part of application No. PCT/US2022/011232, filed on Jan. 5, 2022.

(60) Provisional application No. 63/134,365, filed on Jan. 6, 2021.

(58) Field of Classification Search
CPC ........... G01N 27/3275; G01N 27/4166; G01N 27/4167; G01N 27/4168; G01N 33/098
USPC .................................................. 204/403.01
See application file for complete search history.

(56) References Cited

U.S. PATENT DOCUMENTS

| | | | |
|---|---|---|---|
| 5,464,456 | A | 11/1995 | Kertz |
| 5,819,467 | A | 10/1998 | Zucker |
| 8,289,035 | B1 | 10/2012 | Gensler |
| 8,819,988 | B2 | 9/2014 | Corsi et al. |
| 10,241,097 | B2 | 3/2019 | Miresmailli |
| 10,986,827 | B2 | 4/2021 | Aronov |
| 11,226,306 | B2 | 1/2022 | Burge |
| 2008/0190020 | A1 | 8/2008 | Todd |
| 2013/0255150 | A1 | 10/2013 | Karpinski et al. |
| 2013/0288329 | A1 | 10/2013 | Sanchez et al. |
| 2018/0003687 | A1 | 1/2018 | Minvielle |
| 2018/0267006 | A1 | 9/2018 | Wallbridge et al. |
| 2020/0302338 | A1 | 9/2020 | Carroll |
| 2020/0392736 | A1 | 12/2020 | Zamanzadeh et al. |

FOREIGN PATENT DOCUMENTS

| | | |
|---|---|---|
| JP | 2009-207476 | 9/2009 |
| JP | 2009-278963 | 12/2009 |
| WO | 2011/052203 | 5/2011 |

OTHER PUBLICATIONS

Izumi R., et al., "Biological Information (pH/EC) Sensor Device for Quantitatively Monitoring Plant Health Conditions," 2017 IEEE Sensors, 2017, pp. 1-3, Retrieved from the Internet: URL: https://www.researchgate.net/profile/Hiroki-Ishizuka/publication/322214185_Biological_information_pHEC_sensor_device_for_quantitatively_monitoring_plant_health_conditions/links/61ef7ef09a753545e2f59c7a/Biological-information-pH-EC-sensor-device-for-quantitatively-monitoring-plant-health-conditions.pdf.

Kacira M., et al., "Design and Development of an Automated and Non-contact Sensing System for Continuous Monitoring of Plant Health and Growth ,"Transactions of the ASAE. American Society of Agricultural Engineers, July-Aug. 2001, vol. 44 (4), pp. 989-996, Retrieved from the Internet: URL: https://www.researchgate.net/profile/Murat-Kacira/publication/11345147_Design_and_development_of_an_automated_and_non-contact_sensing_system_for_continuous_monitoring_of_plant_health_and_growth/links/55edc0d708aef55monitoring-of-plant-health-and-growth.pdf.

Keller K., et al., "Nanocellulose Electrodes for Interfacing Plant Electrochemistry," 2016 IEEE Sensors, 2016, pp. 1-3, Retrieved from the Internet: URL: https://ieeexplore.ieee.org/abstract/document/7808846.

Lee B., et al., "Emerging Wearable Sensors for Plant Health Monitoring," Advanced Functional Materials, 2021, vol. 31(52), pp. 1-14, Retrieved from the Internet: URL: https://doi.org/10.1002/adfm.202106475.

Liu Y., et al., "Electrical Impedance Spectroscopy (EIS) in Plant Roots Research: A Review," Plant Methods, Nov. 13, 2021, vol. 17 (Article 118), pp. 1-25, Retrieved from the Internet: URL: https://plantmethods.biomedcentral.com/articles/10.1186/s13007-021-00817-3.

Mourzina Y.G., et al., "Synthesizing Electrodes Into Electrochemical Sensor Systems," Frontiers in Chemistry, Mar. 31, 2021, vol. 9 (Article 641674), pp. 1-13, Retrieved from the Internet: URL: https://www.frontiersin.org/articles/10.3389/fchem.2021.641674/full.

Ricardo De Abreu Silvério Cabrita "Developing an Acquisition System to Sutdy Plant Electrophysiology," Feb. 25, 2016, 97 pages.

Tago S., et al., "Flexible Boron-Doped Diamond (BDD) Electrodes for Plant Monitoring," Sensors, Jul. 15, 2017, vol. 17(7), pp. 1-8.

Yin H., et al., "Soil Sensors and Plant Wearables for Smart and Precision Agriculture," Advanced Materials, 2021, vol. 33 (20), pp. 1-75, Retrieved from the Internet: URL: https://onlinelibrary.wiley.com/doi/am-pdf/10.1002/adma.202007764.

ELECTROCHEMICAL PLANT ACTIVITY MONITOR

CROSS REFERENCE TO RELATED APPLICATION

This application is a continuation-in-part of co-pending U.S. patent application Ser. No. 18/072,011 entitled "ELECTROCHEMICAL PLANT ACTIVITY MONITOR" filed Nov. 30, 2022, which is a continuation-in-part of co-pending PCT Patent Application No. PCT/US22/11232 entitled "ELECTROCHEMICAL PLANT ACTIVITY MONITOR" filed Jan. 5, 2022, which claims the benefit under 35 U.S.C. § 119(c) of U.S. Provisional Application No. 63/134,365 entitled "ELECTROCHEMICAL PLANT ACTIVITY MONITOR" filed Jan. 6, 2021. Both applications are incorporated herein by reference.

TECHNICAL FIELD

The subject disclosure is directed to systems, methods, and apparatus for monitoring the growth and the activity of plants using an electrochemical techniques.

BACKGROUND ART

Assorted variables influence the growth of plants. One major factor for plant growth and development is the soil chemistry of the soil that surrounds the plants. Other important factors include the amount of moisture, ultraviolet (UV) radiation, nitrogen, and other nutrients that can be absorbed into the plants from the surrounding environment. Insufficient nutrient levels will affect plant growth adversely. Excess nutrient levels will either have a similar effect or will simply be wasted. In many instances, local field conditions can determine the quantity of that particular nutrient that is available for consumption by such plants.

Plants use only the nutrients they need and that they are capable of consuming. Consequently, the addition of some nutrients complies with a law of diminishing returns. Above a certain threshold level, a planter obtains little yield response with increasing nutrient level, so that it is important to monitor the absorption of nutrients and the other factors that affect plant growth to ensure that such plants grow in an efficient manner.

From an energy efficiency perspective, nutrients applied above a threshold level are wasted. Similarly, excess amounts of other factors that contribute to growth are also wasted. Accordingly, having the ability to monitor the capacity of a plant to absorb nutrients and other factors will prevent such waste and provide for a more economical use of raw materials.

Additionally, the ability of a plant to absorb moisture, UV and certain nutrients depends upon plant health. Traditionally, the monitoring of plant health has been limited to visual observations or to the use of tools to monitor soil composition. Accordingly, an improved system for monitoring plant health is needed.

DISCLOSURE OF INVENTION

In various implementations, a system for monitoring the activity of a plant containing an aqueous solution and electrolyte therein is provided. A working electrode is inserted into the plant. A standard electrode provides at least one of an electrochemical potential indicating plant activity and a predictable voltage. A data logger connects the working electrode to the standard electrode forming a monitoring system therebetween. The data logger measures the potential difference between the working electrode and the electrolyte within the plant to provide the ability to compare a measured potential difference of the electrochemical cell with a predetermined critical potential difference for the plant.

MODES FOR CARRYING OUT THE INVENTION

Figure 1:
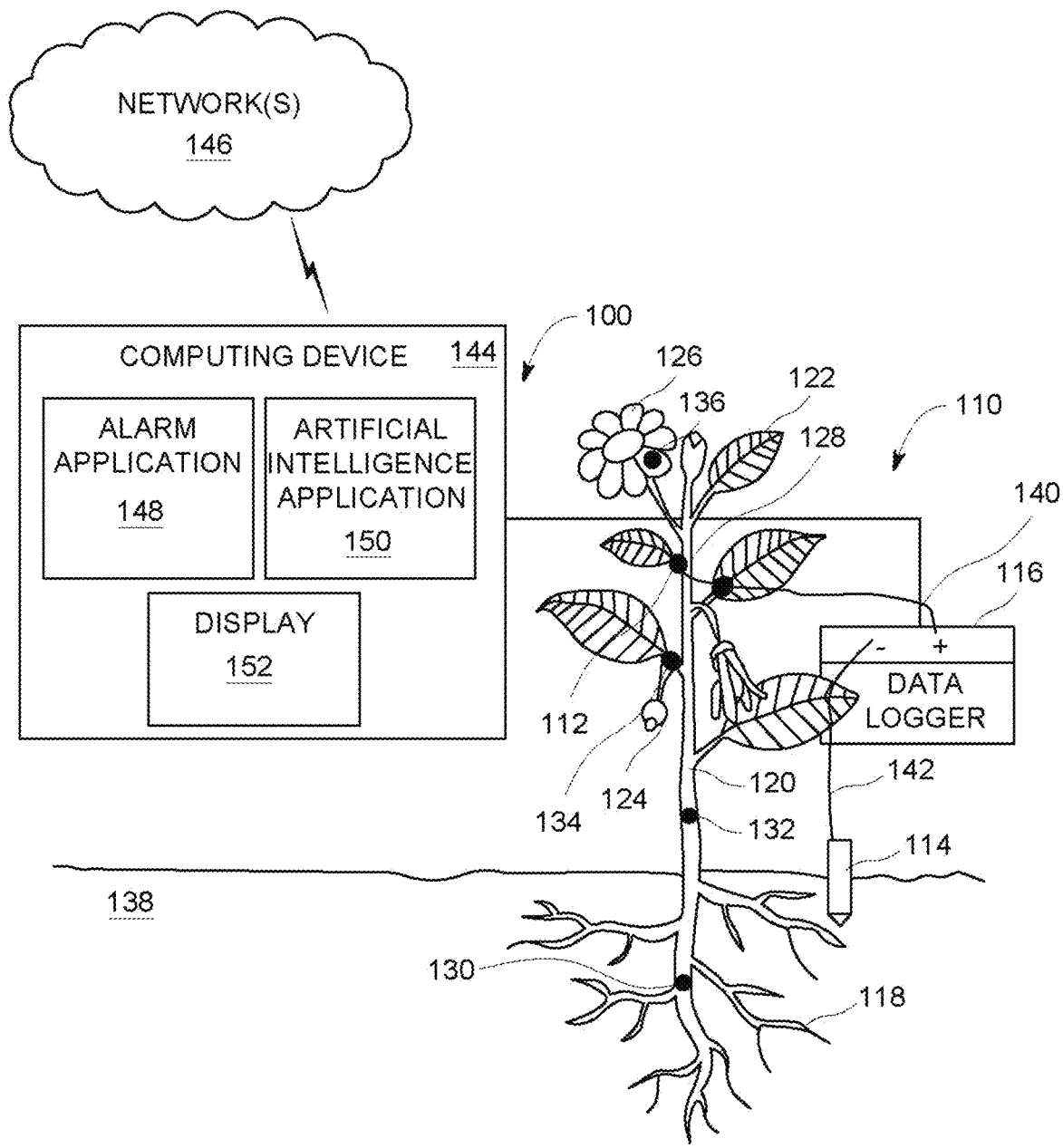
FIG. 1 is a schematic diagram of an embodiment of a passive plant activity monitor in accordance with the disclosed subject matter.

The subject disclosure is directed to systems, methods, and apparatus for monitoring the growth and the activity of plants using an electrochemical techniques. These systems can be used to monitor the health of the plant and its component parts and to detect or to monitor physical, mechanical damage or environmental change in the soil or atmosphere. In other words, the system can use the plant as a sensor to monitor environmental change in the atmosphere or the soil. Additionally, the system can utilize artificial intelligence to detect, to correct, and to mitigate the undesirable changes in health of the plant by using critical electrochemical potential(s) measurements of the plant.

In one embodiment, a passive plant monitor is formed by inserting an electrode into the plant and by inserting a standard electrode into either the surrounding soil or the plant itself. The two electrodes are connected to one another with a data logger to form an electrochemical monitoring system. The potential difference is measured, so that the measured potential difference can be correlated to critical pH levels, UV light exposure, water levels, and/or nutrient levels in the same manner in which medical personnel monitor blood pressure levels in human patients or animals.

In another embodiment, an active plant monitor is formed with the assembled passive plant monitor system by inserting a second pair of electrodes into the soil to inject electrons into the plant. The electrodes can be connected to one another to form a galvanic cell or, in an alternative embodiment, a power supply can be coupled to the electrodes to drive nutrients from soil into the plants. The embodiments of active plant monitors can be configured to kill plants by driving nutrients from the plants into the soil.

Additionally, this electrochemical monitoring system can be used to detect physical damage, mechanical damage, and environmental changes for the surrounding plant or plant components, such as leaves, stems and roots. In other words, we can use the plant with the proposed electrochemical system as a sensor to monitor the environmental change, in soil or atmosphere depending where we insert the electrodes and standard electrodes.

The detailed description provided below in connection with the appended drawings is intended as a description of examples and is not intended to represent the only forms in which the present examples can be constructed or utilized. The description sets forth functions of the examples and sequences of steps for constructing and operating the examples. However, the same or equivalent functions and sequences can be accomplished by different examples.

References to "one embodiment," "an embodiment," "an example embodiment," "one implementation," "an implementation," "one example," "an example" and the like, indicate that the described embodiment, implementation or example can include a particular feature, structure or characteristic, but every embodiment, implementation or example can not necessarily include the particular feature, structure or characteristic. Moreover, such phrases are not necessarily referring to the same embodiment, implementation or example. Further, when a particular feature, structure or characteristic is described in connection with an embodiment, implementation or example, it is to be appreciated that such feature, structure or characteristic can be implemented in connection with other embodiments, implementations or examples whether or not explicitly described.

Numerous specific details are set forth in order to provide a thorough understanding of one or more embodiments of the described subject matter. It is to be appreciated, however, that such embodiments can be practiced without these specific details.

Various features of the subject disclosure are now described in more detail with reference to the drawings, wherein like numerals generally refer to like or corresponding elements throughout. The drawings and detailed description are not intended to limit the claimed subject matter to the particular form described. Rather, the intention is to cover all modifications, equivalents and alternatives falling within the spirit and scope of the claimed subject matter.

The disclosed system for monitoring the health of a plant utilizes an electrode that can be inserted into the plant, itself, to monitor electrolyte activity within the plant in the same manner in which a doctor monitors the blood of a human patient. The system can be used in various types of commercial and residential sites, such as traditional farms, industrial farms, urban farms, botanical gardens, large nurseries, universities, or government departments. The system can be used in any type of region in which vegetation is grown, such as forests, grasslands, tundra, deserts, and ice sheets.

The electrode can be inserted anywhere in the plant, including the stem, the leaf, the roots, or other parts of the plant. Once the electrode is inserted, a data logger or other similar device measures the potential difference between the inserted electrode and a standard voltage source. The potential difference can be correlated to the health of the plant, so that a change in potential difference can be related to a certain deficiency or condition that affects the health of the plant. In other words, the measured potential difference can be correlated to critical pH levels, UV light exposure, water levels, and/or nutrient levels.

The system can be configured with an alarm to alert the planter of the need to increase or to decrease nutrients, UV, water, or PH. The system can be configured to send a wireless signal through a network to indicate if the plant is dying.

The system can collect electrical potential data for analysis by a human or by artificial intelligence. The artificial intelligence can be used to manage the system to activate and to grow the plant based on critical potentials. The system can save the data and can submit a recommended action, wirelessly, to correct the situation and mitigate the plant problems on time and immediately when there is a problem.

In another embodiment, a second set of electrodes can be inserted into the soil to inject electrons into the plant. The second set of electrodes can be connected to one another to form a galvanic cell. Alternatively, a power supply can be coupled to the electrodes to drive nutrients from soil into the plants to correct any deficiencies.

The disclosed system can be used to measure electrochemical potential of the electrochemical cell. The measured electrochemical potential has been determined to correlate to the Oxygen Reduction Potential (ORP) in plants.

The ORP measures the ability of a substance (like tree sap or soil around tree roots) to oxidize or reduce. This is directly linked to the chemical processes happening within the tree. Changes in ORP can indicate stress in trees, such as drought, disease, or nutrient deficiencies. These stresses can alter the chemical balance in the tree, reflected in the ORP values.

The use of ORP monitoring in trees, utilizing platinum and copper/copper sulfate electrodes represents an approach to measuring and to managing tree health. The disclosed system provides real-time, in-situ data that can be crucial for early detection of stressors, enabling more effective and timely interventions. The system has applications in forestry, agriculture, and environmental monitoring, aiding in the conservation and management of tree populations.

Referring now to the drawings and, in particular, to FIG. 1, there is shown a passive system, generally designated by the numeral 100, for monitoring the activity (i.e., health) of a plant 110. In some embodiments, the system 100 can be used to monitor the health of the plant 110, so that actions can be taken to improve the health of the plant 110. In other embodiments, the actions can be taken to control the growth of the plant 110 or to kill the plant 110.

The system 100 includes a working electrode 112, a standard electrode 114, and a data logger 116. The plant 110 includes roots 118, a stem 120, leaves 122, seeds 124, and flowers 126. The plant 110 can include an aqueous solution and an electrolyte therein. The system 100 can be used to detect or monitor physical, mechanical damage or environmental change in the soil or atmosphere depending upon the placement/insertion of the working electrode 112 and/or the standard electrode 114. In some embodiments, the plant 110 can be used as a sensor for soil conditions and/or atmospheric conditions.

The working electrode 112 can be inserted directly into the plant 110. The working electrode 112 can be configured to create one or more bore holes to form stations 128-136 on the plant 110 to facilitate insertion therein. Alternatively, the bore holes can be created via drilling, punching, puncturing, or other similar hole-creating operations. In some embodiments, multiple working electrodes (not shown) can be inserted into the bore holes at the stations 128-134.

The standard electrode 114 can be inserted into the plant 110 and/or into the soil 138 that surrounds the plant 110. The data logger 116 can connect the working electrode 112 to the standard electrode 114 to form an electrochemical cell to measure electrochemical potential. In this exemplary embodiment, the working electrode 112 inserts into the plant stem 120 at the station 128. In other embodiments, the working electrode 112 can be inserted into the bore holes at the stations 130-136, as necessary. It should be understand that the soil 138 can be replaced by other plant growth media in some embodiments.

Once the electrochemical cell is formed, the data logger 116 can be used to measure the potential difference between the working electrode 112 and the electrolyte inside the plant 110. The data logger 116 can be monitored for changes in the measured potential difference. The data logger 116 provides the ability to compare a measured potential with a predetermined critical potential difference for the plant 110. Additionally, the data logger 116 can be configured to save data and/or to submit a recommended action through an immediate wireless communication, so that the system 100 can inform the user of problems in a timely manner. The recommended action can provide a user with the ability to correct the problem or to mitigate the problem.

A change in the measured potential difference can indicate a change in soil chemistry and/or pH, a change in the amount of sun or UV radiation that the plant 110 is receiving, a change in the amount of water that the plant 110 is receiving and/or a change in the amount of nutrients that are being absorbed from the soil 138.

As indicated above, the measured electrochemical potential has been determined to correlate to the ORP of the plant 110. The measured ORP can be used to determine the extent to which oxidation or reduction of electrolyte is occurring within plants and trees, including plant 110.

In some exemplary embodiments, ORP is measured directly in the plant 110 with the working electrode 112 being formed from platinum. The use of platinum prevents the working electrode 112 from reacting with the redox substances in tree sap or surrounding soil. Platinum is highly stable and inert, providing consistent and reliable measurements.

The units for ORP measurements are typically measured in millivolts (mV), as shown in Table 1. Higher levels of oxygen in the electrolyte in the plant 110 correlate to higher ORP measurements. The ORP measurements can be above zero or below zero.

Oxygen production in trees and plants primarily occurs through photosynthesis (in the leaves). The process requires light and involves the oxidation of water, releasing oxygen as a by-product. A more negative ORP value correlates to conditions that are less favorable for the oxidation reactions involved in photosynthesis, potentially leading to reduced oxygen production.

A significantly negative ORP measurement indicates strongly reducing environment. In such conditions, the environment is less conducive to oxidative processes, such as oxygen production in photosynthesis. For a Banyan tree that is subject to an agricultural treatment, it has been determined that an ORP measurement of above −0.45 indicates that the agricultural treatment is not working.

Baseline measurements for tomato, pear, and apple plants have been obtained. The measurements can be used to observe trends and to determine the health of such plants, as well.

The working electrode 112 can include one or more oxidation resistant materials. Oxidation resistant materials can include various forms of carbon, noble metals, noble metal alloys, high performance alloys and stainless steel alloys. Suitable forms of carbon can include graphite, carbon nanotubes, graphene, carbon black, activated carbon, and fullerenes. Such exemplary forms of conductive carbon include single walled carbon nanotubes, multiwalled carbon nanotubes, carbon blacks of various surface areas, and other related materials. Suitable noble metals and noble metal alloys can include gold, platinum, silver, palladium, iridium, rhodium, and ruthenium or alloys of gold, platinum, silver, palladium, iridium, rhodium, or ruthenium. Noble metals can include metals that have filled electronic d-bands.

The standard electrode 114 can be an electrode that provides a voltage that is predictable under certain conditions, such as temperature and pressure. In particular, the standard electrode 114 can be an electrode that has a stable and well-known electrode potential, such as an electrode that utilizes a redox system with constant (buffered or saturated) concentrations of each participant of the redox reaction. In some embodiments, the standard electrode 114 can be a reference electrode. In other embodiments, the standard electrode 114 can be a quasi-reference electrode or a pseudo-reference electrode, which has potential that varies predictably with conditions.

Exemplary reference electrodes include copper-copper(II) sulfate electrodes and silver/silver chloride electrodes, such as a MCM McMiller reference electrode that includes a rugged ceramic plug having a conical shaped surface that is designed for use in soft soils. Such electrodes include a high purity copper rod and a robust polycarbonate tube. In some embodiments, solid state electrodes can be used. The use of copper-copper(II) sulfate electrodes provides a stable reference potential against which a platinum electrode potential can be measured.

The geometric configuration of the electrochemical cell is not critical. The working electrode 112 and the standard electrode 114 can have any suitable geometric configuration. The working electrode 112 and the standard electrode 114 can include one or more leads 140-142. The working electrode 112, the standard electrode 114, and/or the leads 140-142 can be in the form of wire, mesh, foil, an ingot, sheet or wire. The leads 140-142 can be flexible, semi-rigid, or rigid members.

The data logger 116 can determine the potential difference between the working electrode 112 and the electrolyte. In other embodiments, the data logger 116 can include an ammeter, a voltmeter, a multi-meter, a multi-tester, and an electronic measuring instrument that combines several measurement functions in one unit. The system can include a data logger to monitor and transmit the data wirelessly. Exemplary data loggers include Graphtec midi Data Loggers provided by Dataq Instruments Inc. of Akron, Ohio.

As shown in FIG. 1, the data logger 116 can be coupled to a computing device 144, which can be coupled to one or more external networks 146. In some embodiments, the computing device 144 can facilitate the collection of and the display of data relating to the activity of the plant 210. In other embodiments, the computing device 244 can include software applications and/or apps to analyze the activity of the plant 210.

Network(s) 146 can be implemented by any type of network or combination of networks including, without limitation: a wide area network (WAN) such as the Internet, a local area network (LAN), a Peer-to-Peer (P2P) network, a telephone network, a private network, a public network, a packet network, a circuit-switched network, a wired network, and/or a wireless network. Computing device 144 and/or data logger 116 can communicate via network 146 using various communication protocols (e.g., Internet communication protocols, WAN communication protocols, LAN communications protocols, P2P protocols, telephony protocols, and/or other network communication protocols), various authentication protocols, and/or various data types (web-based data types, audio data types, video data types, image data types, messaging data types, signaling data types, and/or other data types).

The computing device 144 can include an alarm software application 148, an artificial intelligence application 150, and a display 152. The alarm software application 148 can be configured to activate an alarm when the electrical potential that is measured by the data logger 116 either increases by a predetermined threshold or decreases by a predetermined threshold. The alarm can include an audible sound and/or a visual effect displayed on the display 152.

The predetermined threshold(s) can be correlated to increases or to decreases in critical pH levels, UV light exposure, water levels, and/or nutrient levels. The correlations can be identified by a human data analyst and/or by the artificial intelligence application 150.

The artificial intelligence application 150 can be any suitable artificial intelligence application, including applications that are based on Open Source Computer Vision Library (OpenCV) algorithms or functions, Vision-something-Library (VXL) algorithms or functions, AForge.NET algorithms or functions, and/or LTI-Lib algorithms or functions. In some embodiments, the artificial intelligence application 150 can utilize TensorFlow, Caffe, MATLAB Image Processing Toolbox, Computer Vision by Microsoft, Google Cloud Vision, Google Colaboratory (Colab) frameworks or platforms. In other embodiments, the artificial intelligence application 150 can utilize neural networks.

It should be understood that in some embodiments, the placement of sensors should be predetermined to ensure accurate readings (e.g., at various depths in the soil or different parts of the tree). Further, in some embodiments, ORP data must be carefully analyzed in the context of other environmental and physiological parameters. Regular calibration of electrodes can enhance the accuracy of readings, especially in varying environmental conditions It should be understood that embodiments are contemplated that include a plurality of electrodes inserted into a plurality of stations within the plant 110. The electrodes can be permanently connected to leads or configured for releasable connections to disconnect and to reconnect leads to take facilitate measurements at multiple stations on the plant 110. These electrodes and leads can be configured for wireless connection to the data logger 116 and/or the computing device 144 to provide a comprehensive profile of the health of the plant 110.

Figure 2:
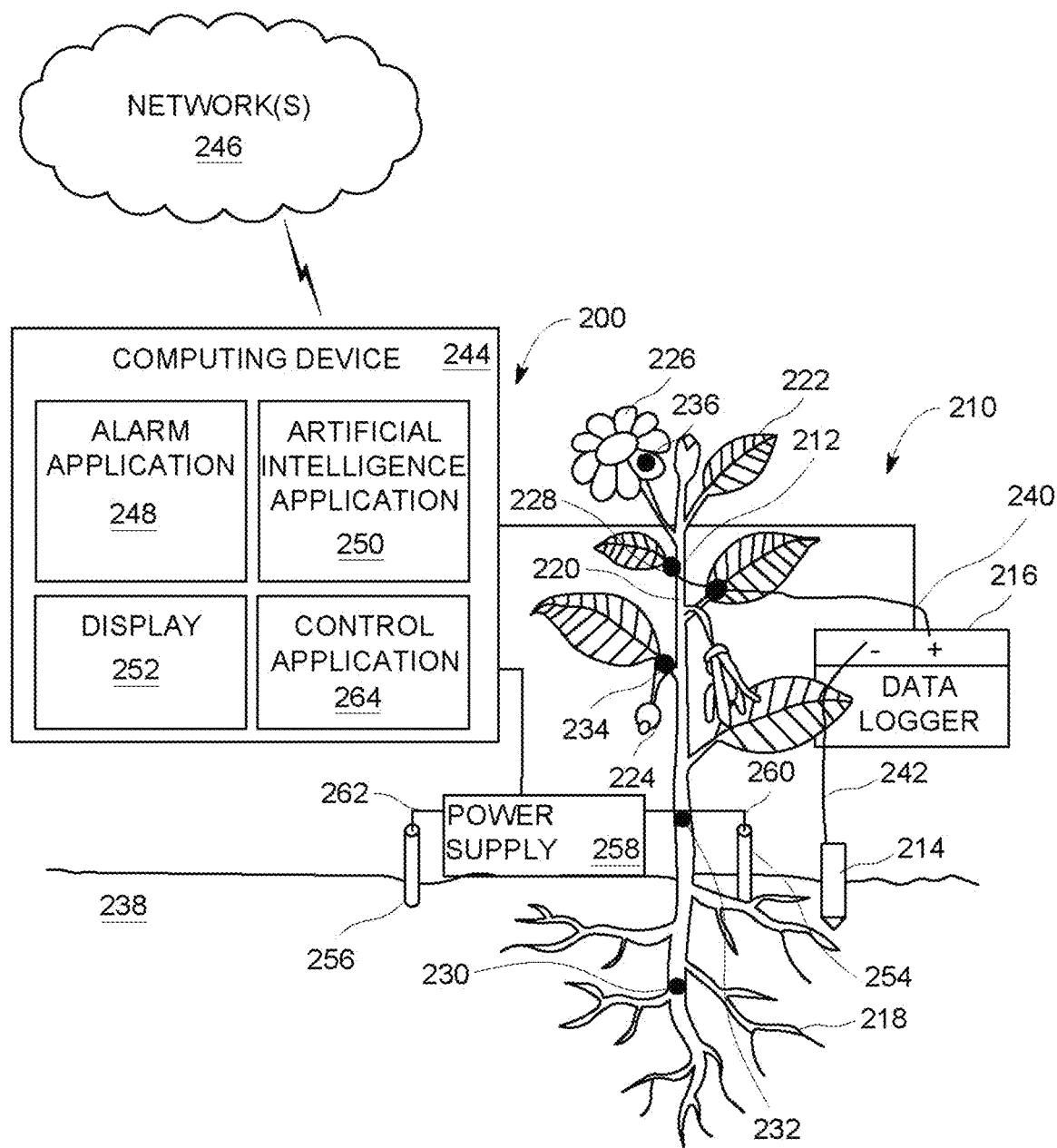
FIG. 2 is a schematic diagram of an embodiment of an active plant activity monitor in accordance with the disclosed subject matter.

Referring now to FIG. 2 with continuing reference to the foregoing figure, another embodiment of a plant activity monitoring system, generally designated by the numeral 200, is shown. Like the embodiment shown in FIG. 1, the system 200 is adapted to monitor the activity (i.e., health) of a plant 210. Similarly, the system 200 includes a working electrode 212, a standard electrode 214, and a data logger 216. The plant 210 includes roots 218, a stem 220, leaves 222, seeds 224, and flowers 226. The plant 210 can include an aqueous solution and an electrolyte therein.

The working electrode 212 can be inserted into the plant 210 at various stations 228-236 to monitor the internal electrolyte in the plant 210. The standard electrode 214 can be inserted into growth media or soil 238 that surrounds the plant 210 or, alternatively, into the plant 210, itself. The data logger 216 can connect the working electrode 212 to the standard electrode 214 with leads 240-242 to form a first electrochemical cell.

The metering device 216 can communicate with a computing device 244, which can be coupled to a network 246. The computing device 244 can include an alarm application 248, an artificial intelligence application 250, and a display 252.

Unlike the embodiment shown in FIG. 1, the system 200 is an active plant monitor that includes a driving electrode 254 and a counter electrode 256 that inject electrons into the plant 210. The driving electrode 254 and the counter electrode 256 can be connected to a power supply 258 with a pair of leads 260-262 to form a second electrochemical cell. The power supply 258 can supply power to the second electrochemical cell to manipulate the electrochemistry of the plant 210 by driving nutrients from the soil 238 into the plant 210.

In this exemplary embodiment, the power supply 258 includes a DC power source. The DC power source can be a battery, such as a rechargeable battery, a wind power source, a natural gas generator, or other similar power source. In some embodiments, the power supply 258 can receive power from a solar cell.

In other embodiments, the DC power source can be coupled to an AC power source with a transformer positioned therebetween to convert AC power into DC power. The transformer can include a rectifier and a diode stack.

The computing device 244 can be coupled to the data logger 216 to perform functions to control the second electrochemical cell, including the power supply 258, and to determine the potential difference between the working electrode 212 and the counter electrode 214. It should be understood that a computing device (not shown) that is similar to computing device 244 can be coupled to the data logger 116 to form the functions of the system 100 shown in FIG. 1.

The selection of materials for the driving electrode 254 and the counter electrode 256 will depend upon such factors as plant type for plant 210, soil or growth media chemistry, and the type of nutrients that will be driven into (or out of) the plant 210.

The selection of materials will be informed by the galvanic series, which determines the electrochemical potential and nobility of metals and metal alloys. When two electrically connected metals are submerged in an electrolyte, the less noble metal will become an anode and the other electrode will become the cathode. For example, when a cathode is formed from stainless steel, an anode can be formed from metals that are below stainless steel on the galvanic series. Such metals can include indium, aluminum, uranium, cadmium, beryllium, zinc, magnesium, and/or alloys that include one or more of those metals.

In some embodiments, the computing device 244 includes a control application 264 for controlling the power supply 258. The control application 264 can cooperate with the artificial intelligence application 250, so that optimal control routines can be developed to control the system 200 automatically. In other embodiments, the control application 264 can be directed by a human operator.

Figure 3:
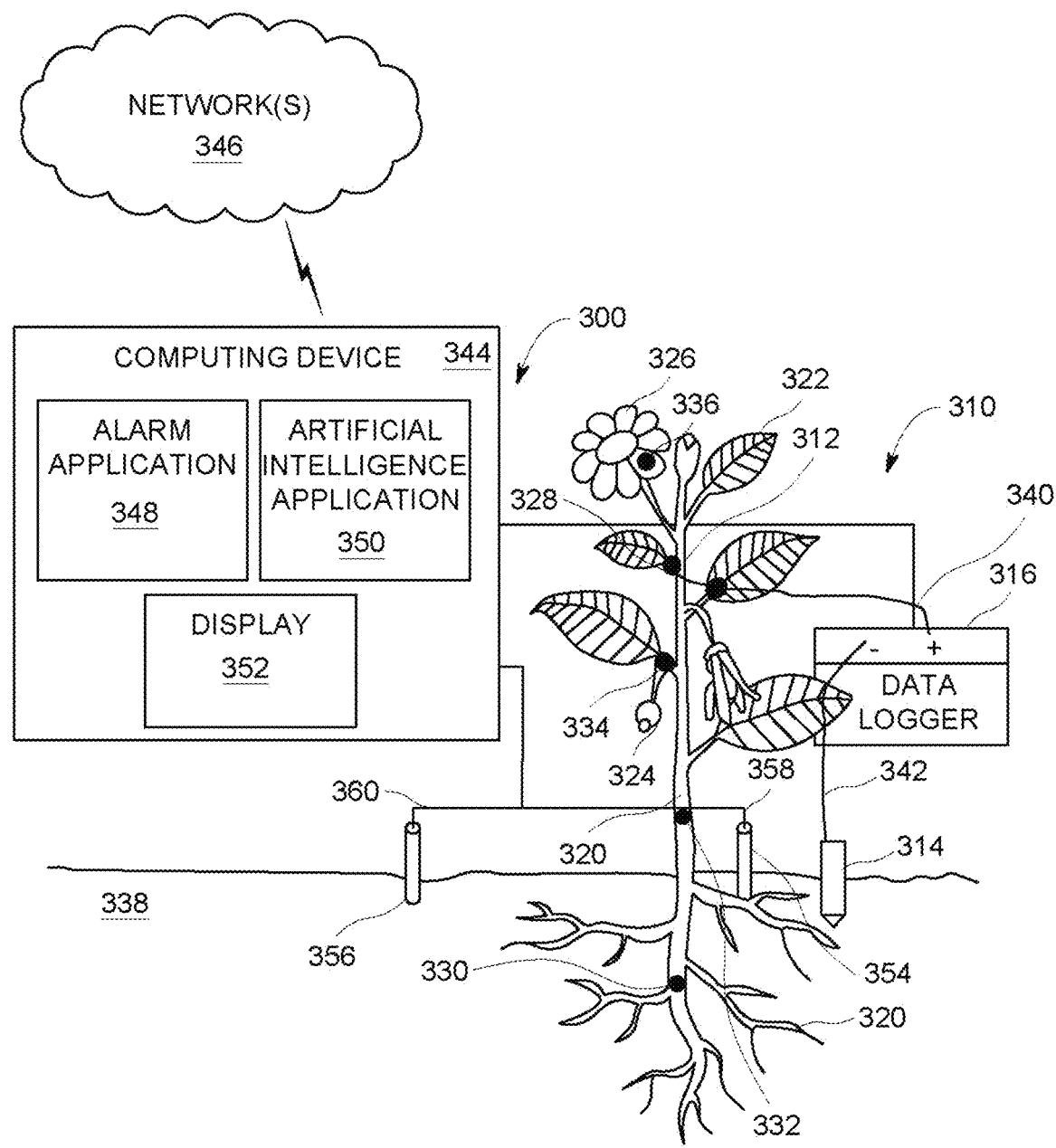
FIG. 3 is a schematic diagram of another embodiment of an active plant activity monitor in accordance with the disclosed subject matter.

Referring now to FIG. 3 with continuing reference to the foregoing figures, another embodiment of a plant activity monitoring system, generally designated by the numeral 300, is shown. Like the embodiments shown in FIGS. 1-2, the system 300 is adapted to monitor the activity (i.e., health) of a plant 310. Similarly, the system 300 includes a working electrode 312, a standard electrode 314, and a data logger 316. The plant 310 includes roots 318, a stem 320, leaves 322, seeds 324, and flowers 326. The plant 310 can include an aqueous solution and an electrolyte therein.

The working electrode 312 can be inserted into the plant 310 at various stations 328-336 to monitor the internal electrolyte in the plant 310. The standard electrode 314 can be inserted into growth media or soil 338 that surrounds the plant 310 or, alternatively, into the plant 310, itself. The data logger 316 can connect the working electrode 312 to the standard electrode 314 with leads 340-342 to form a first electrochemical cell.

The metering device 316 can communicate with a computing device 344, which can be coupled to a network 346. The computing device 344 can include an alarm application 348, an artificial intelligence application 350, and a display 352.

Unlike the embodiment shown in FIG. 1, the system 300 is an active plant monitor that includes a driving electrode 354 and a counter electrode 356 that inject electrons into the plant 310. Unlike the embodiment shown in FIG. 2, the driving electrode 354 is connected to the counter electrode 356 with the leads 358-360. The system 310 does not include a power supply, like the power supply 258 shown in FIG. 2, because the driving electrode 354 and the counter electrode 356 form a galvanic cell.

The selection of materials for the driving electrode 354 and the counter electrode 356 will depend upon such factors as plant type for plant 310, soil or growth media chemistry, and the type of nutrients that will be driven into (or out of) the plant 310.

The selection of materials will be informed by the galvanic series, which determines the electrochemical potential and nobility of metals and metal alloys. When two electrically connected metals are submerged in an electrolyte, the less noble metal will become an anode and the other electrode will become the cathode. For example, when a cathode is formed from stainless steel, an anode can be formed from metals that are below stainless steel on the galvanic series. Such metals can include indium, aluminum, uranium, cadmium, beryllium, zinc, magnesium, and/or alloys that include one or more of those metals.

Figure 4:
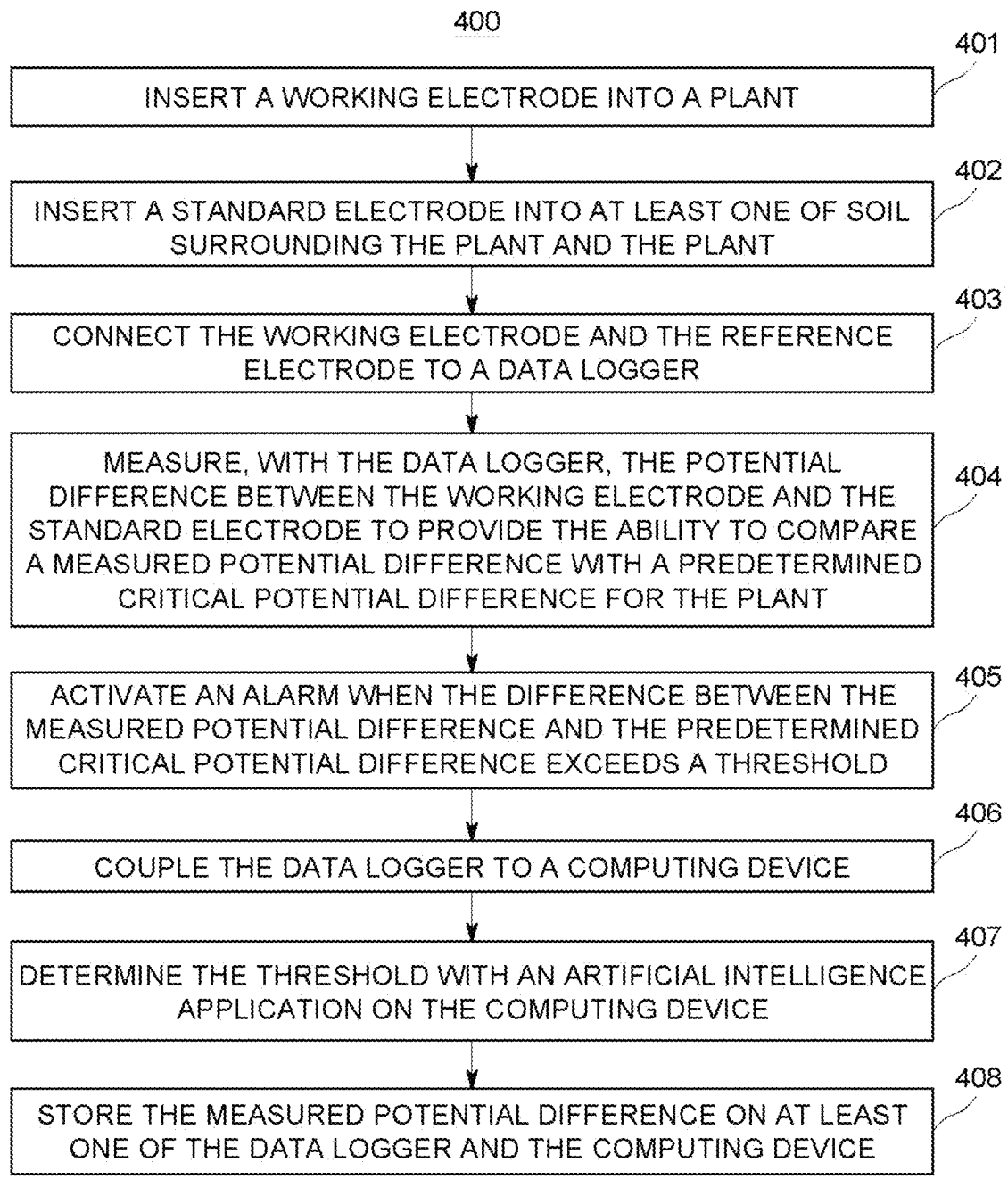
FIG. 4 is an exemplary process in accordance with the disclosed subject matter.

Referring now to FIG. 4 with continuing reference to the foregoing figures, an exemplary method, generally designated with the numeral 400, for monitoring the growth of a plant is shown. The method 400 can be performed using the system 100 on the plant 110 shown in FIG. 1, the system 200 on the plant 210 shown in FIG. 2, and/or the system 300 on the plant 310 shown in FIG. 3.

At 401, a working electrode is inserted into a plant. In this exemplary embodiment, the working electrode can be the working electrode 112 shown in FIG. 1, the working electrode 212 shown in FIG. 2 and/or the working electrode 312 shown in FIG. 3.

At 402, a standard electrode is inserted into at least one of soil surrounding the plant and the plant. In this exemplary embodiment, the standard electrode can be the standard electrode 114 shown in FIG. 1, the standard electrode 214 shown in FIG. 2, and/or the standard electrode 314 shown in FIG. 3.

At 403, the working electrode and the reference electrode is connected to a data logger. In this exemplary embodiment, the data logger can be the data logger 116 shown in FIG. 1, the data logger 216 shown in FIG. 2, and/or the data logger 316 shown in FIG. 3.

At 404, the potential difference between the working electrode and the standard electrode is measured with the data logger to provide the ability to compare a measured potential difference with a predetermined critical potential difference for the plant. The measured potential difference and/or the predetermined critical potential difference can be correlated to a predetermined amount of water (i.e., moisture) within the plant, to ultraviolet radiation directed toward the plant, to the absence or to the presence of nutrients in the plant, and to the pH level of the soil surrounding the plant.

At 405, an alarm is activated when the difference between the measured potential difference and the predetermined critical potential difference exceeds a threshold. In this exemplary embodiment, the alarm can be activated by the alarm application 148 shown in FIG. 1, the alarm application 248 shown in FIG. 2, and/or the alarm application 348 shown in FIG. 3.

At 406, the data logger is coupled to a computing device. In this exemplary embodiment, the computing device can be the computing device 144 shown in FIG. 1, the computing device 244 shown in FIG. 2, and/or the computing device 344 shown in FIG. 3.

At 407, an artificial intelligence application on the computing device determines the threshold. In this exemplary embodiment, the artificial intelligence application can be the artificial intelligence application 150 shown in FIG. 1, the artificial intelligence application 250 shown in FIG. 2, and/or the artificial intelligence application 350 shown in FIG. 3.

At 408, the measured potential difference is stored on at least one of the data logger and the computing device.

Figure 5:
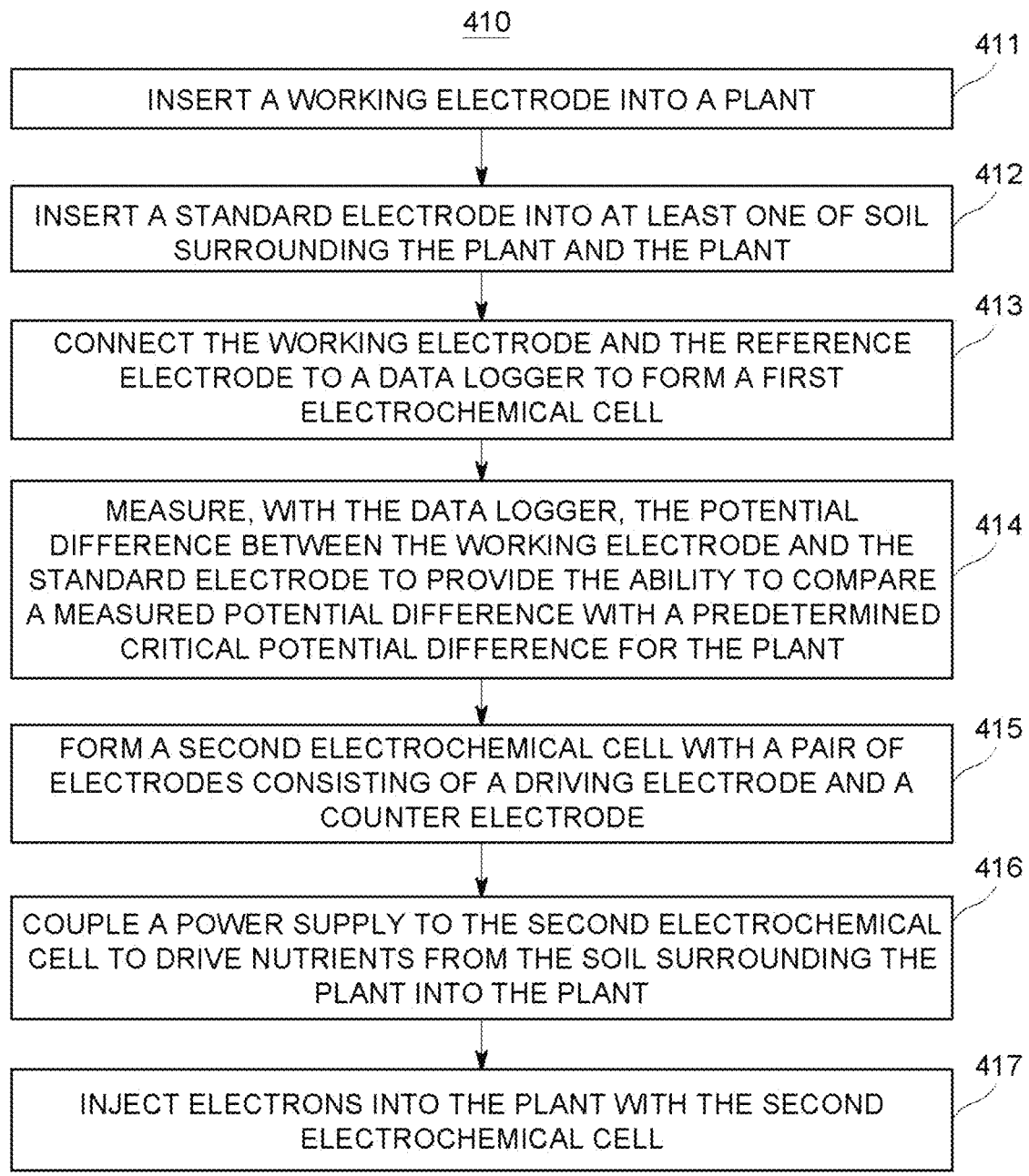
FIG. 5 is another exemplary process in accordance with the disclosed subject matter.

Referring now to FIG. 5 with continuing reference to the foregoing figures, an exemplary method, generally designated with the numeral 410, for monitoring the growth of a plant is shown. Unlike the method 400, the method 410 can be used for active monitoring of the plant. The method 410 can be performed using the system 200 on the plant 210 shown in FIG. 2, and/or the system 300 on the plant 310 shown in FIG. 3.

At 411, a working electrode is inserted into a plant. In this exemplary embodiment, the working electrode can be the working electrode 212 shown in FIG. 2 and/or the working electrode 312 shown in FIG. 3.

At 412, a standard electrode is inserted into at least one of soil surrounding the plant and the plant. In this exemplary embodiment, the standard electrode can be the standard electrode 214 shown in FIG. 2, and/or the standard electrode 314 shown in FIG. 3.

At 413, the working electrode and the reference electrode are connected to a data logger to form a first electrochemical cell. In this exemplary embodiment, the data logger can be the data logger 216 shown in FIG. 2, and/or the data logger 316 shown in FIG. 3.

At 414, the potential difference between the working electrode and the standard electrode is measured with the data logger to provide the ability to compare a measured potential difference with a predetermined critical potential difference for the plant.

At 415, a second electrochemical cell is formed with a pair of electrodes consisting of a driving electrode and a counter electrode. In this exemplary embodiment, the driving electrode can be the driving electrode 254 shown in FIG. 2 and/or the driving electrode 354 shown in FIG. 3. The counter electrode can be the counter electrode 256 shown in FIG. 2 and/or the counter electrode 356 shown in FIG. 3.

At 416, a power supply is coupled to the second electrochemical cell to drive nutrients and moisture from the soil surrounding the plant into the plant. In this exemplary embodiment, the power supply can be the power supply 258 shown in FIG. 2. This step is not required with the system 300 shown in FIG. 3 because the driving electrode 354 and the counter electrode 356 form a galvanic cell.

At 417, ions are injected into the plant with the second electrochemical cell. The injection of electrons can drive nutrients in to the plant. Exemplary nutrients include phosphate, sodium, calcium, and nitrogen ions. Phosphorus and nitrogen are key nutrients that plants need and can be limiting factors in crop yields. Maintaining the proper levels of phosphorous and nitrogen in the plants provides such plants with the ability to acquire energy, to store energy, and to transfer the energy throughout the plants. Phosphorous and nitrogen also promote the development of roots, flowers and fruit, especially essential for showy ornamental plants or for vegetables grown for consumption.

Figure 6:
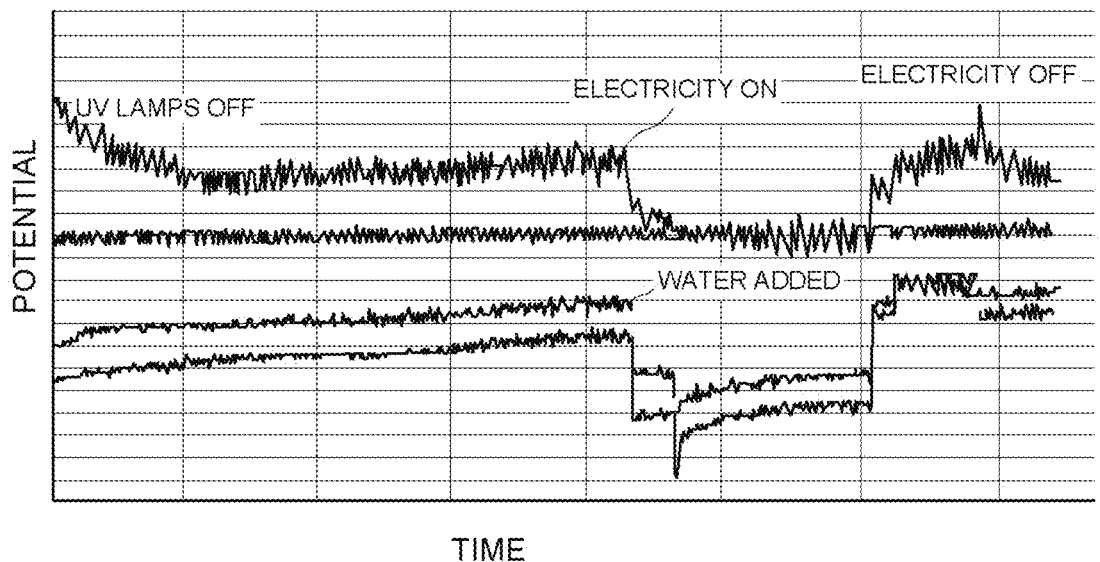
FIG. 6 is a plot of the relationship between electrical potential vs. time.
Figure 7:
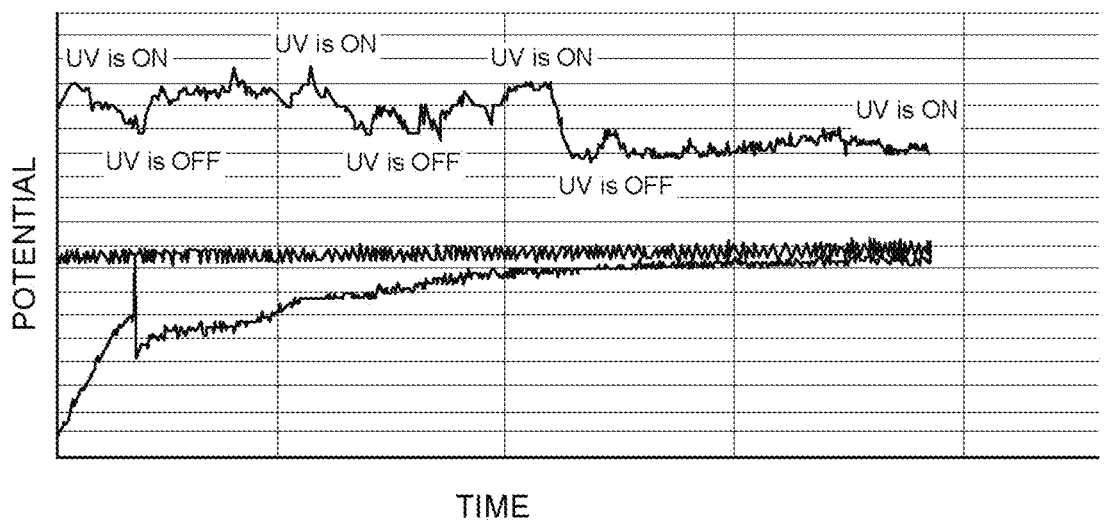
FIG. 7 is another plot of the relationship between electrical potential vs. time.
Figure 8:
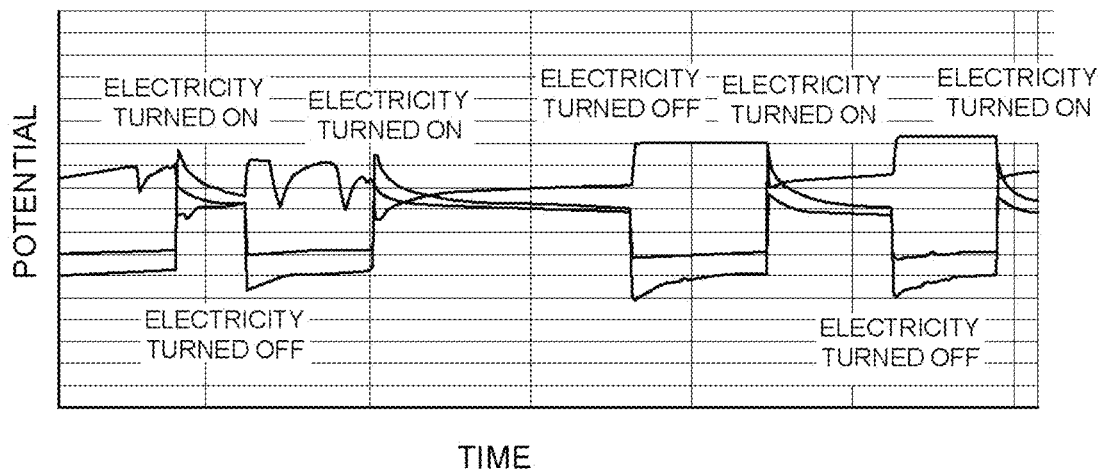
FIG. 8 is another plot of the relationship between electrical potential vs. time

Exemplary potential difference plots as a function of time that were obtained through the performance of method 400 and/or method 410 are shown in FIGS. 6-10. FIG. 6 illustrates the effect of changing UV exposure, water content, and applied electricity on the measured potential difference as a function of time. FIG. 7 illustrates the effect of changing UV exposure on the measured potential difference as a function of time. FIG. 8 illustrates the effect of changing applied electricity on the measured potential difference as a function of time.

Figure 9:
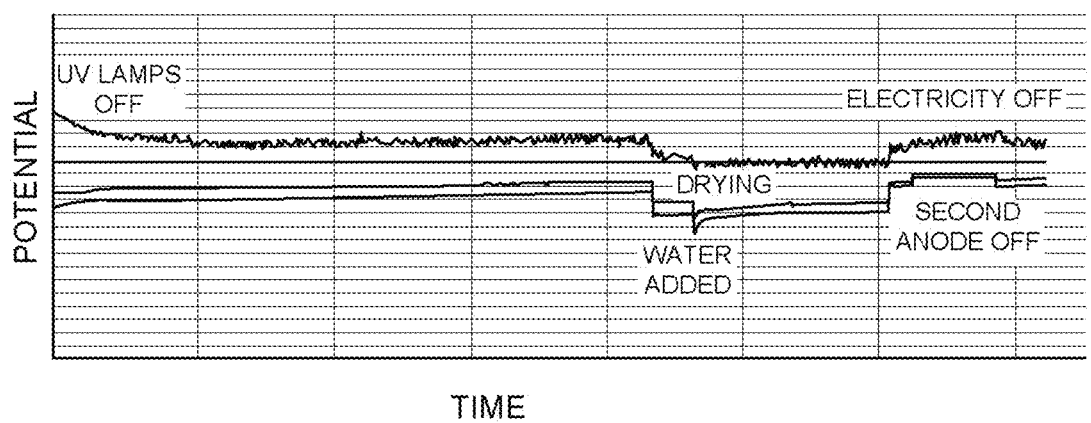
FIG. 9 is another plot of the relationship between electrical potential vs. time.
Figure 10:
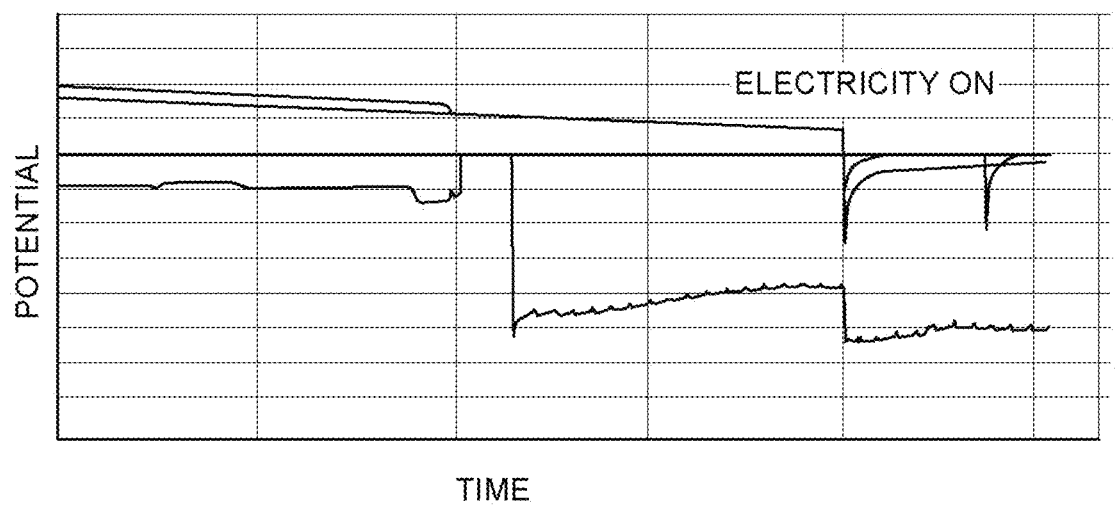
FIG. 10 is another plot of the relationship between electrical potential vs. time.

FIG. 9 also illustrates the effect of changing UV exposure, water content, and applied electricity on the measured potential difference as a function of time. FIG. 10 also illustrates the effect of changing applied electricity on the measured potential difference as a function of time.

Exemplary Computing Device

Figure 11:
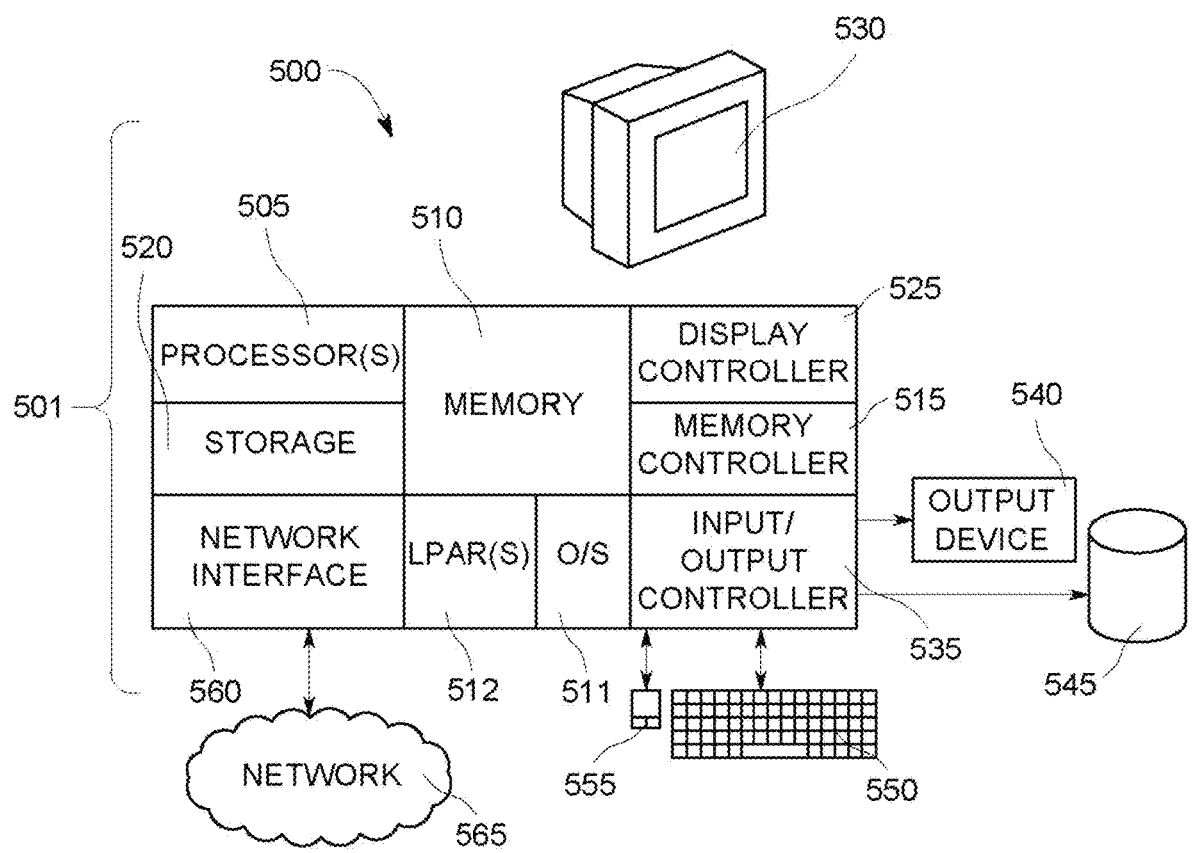
FIG. 11 is a schematic diagram of an exemplary computing device in accordance with this disclosure.

Referring now to FIG. 11 with continuing reference to the forgoing figures, an exemplary computing device is generally shown. The exemplary computing device can be the computing device 144 shown in FIG. 1, the computing device 244 shown in FIG. 2 and/or the computing device 344 shown in FIG. 3. The system and/or device described herein can be implemented in hardware, software (e.g., firmware), or a combination thereof. In an exemplary embodiment, the methods described herein are implemented in hardware as part of the microprocessor of a special or general-purpose digital computer, such as a personal computer, workstation, minicomputer, or mainframe computer. The system 500 therefore can include general-purpose computer or mainframe 501 capable of running multiple instances of an O/S simultaneously.

In an exemplary embodiment, in terms of hardware architecture, as shown in FIG. 11, the computer 501 includes one or more processors 505, memory 510 coupled to a memory controller 515, and one or more input and/or output (I/O) devices 540, 545 (or peripherals) that are communicatively coupled via a local input/output controller 535. The input/output controller 535 can be, for example but not limited to, one or more buses or other wired or wireless connections, as is known in the art. The input/output controller 535 can have additional elements, which are omitted for simplicity, such as controllers, buffers (caches), drivers, repeaters, and receivers, to enable communications. Further, the local interface can include address, control, and/or data connections to enable appropriate communications among the aforementioned components. The input/output controller 535 can include a plurality of sub-channels configured to access the output devices 540 and 545. The sub-channels can include fiber-optic communications ports.

The processor 505 is a hardware device for executing software, particularly that stored in storage 520, such as cache storage, or memory 510. The processor 505 can be any custom made or commercially available processor, a central processing unit (CPU), an auxiliary processor among several processors associated with the computer 501, a semiconductor based microprocessor (in the form of a microchip or chip set), a macroprocessor, or generally any device for executing instructions.

The memory 510 can include any one or combination of volatile memory elements (e.g., random access memory (RAM, such as DRAM, SRAM, SDRAM, etc.)) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 510 can incorporate electronic, magnetic, optical, and/or other types of storage media. Note that the memory 510 can have a distributed architecture, where various components are situated remote from one another, but can be accessed by the processor 505.

The instructions in memory 510 can include one or more separate programs, each of which comprises an ordered listing of executable instructions for implementing logical functions. In the example of FIG. 11, the instructions in the memory 510 a suitable operating system (OS) 511. The operating system 511 essentially controls the execution of other computer programs and provides scheduling, input-output control, file and data management, memory management, and communication control and related service.

The memory 510 can include multiple logical partitions (LPARs) 512, each running an instance of an operating system. The LPARs 512 can be managed by a hypervisor, which can be a program stored in memory 510 and executed by the processor 505.

In an exemplary embodiment, a conventional keyboard 550 and mouse 555 can be coupled to the input/output controller 535. Other output devices such as the I/O devices 540, 545 can include input devices, for example but not limited to a printer, a scanner, microphone, and the like. Finally, the I/O devices 540, 545 can further include devices that communicate both inputs and outputs, for instance but not limited to, a network interface card (NIC) or modulator/demodulator (for accessing other files, devices, systems, or a network), a radio frequency (RF) or other transceiver, a telephonic interface, a bridge, a router, and the like. The system 500 can further include a display controller 525 coupled to a display 530. In an exemplary embodiment, the system 500 can further include a network interface 560 for coupling to a network 565. The network 565 can be an IP-based network for communication between the computer 501 and any external server, client and the like via a broadband connection. The network 565 transmits and receives data between the computer 501 and external systems. In an exemplary embodiment, network 565 can be a managed IP network administered by a service provider. The network 565 can be implemented in a wireless fashion, e.g., using wireless protocols and technologies, such as WiFi, WiMax, etc. The network 565 can also be a packet-switched network such as a local area network, wide area network, metropolitan area network, Internet network, or other similar type of network environment. The network 565 can be a fixed wireless network, a wireless local area network (LAN), a wireless wide area network (WAN) a personal area network (PAN), a virtual private network (VPN), intranet or other suitable network system and includes equipment for receiving and transmitting signals.

If the computer 501 is a PC, workstation, intelligent device or the like, the instructions in the memory 510 can further include a basic input output system (BIOS) (omitted for simplicity). The BIOS is a set of essential software routines that initialize and test hardware at startup, start the OS 511, and support the transfer of data among the hardware devices. The BIOS is stored in ROM so that the BIOS can be executed when the computer 501 is activated.

When the computer 501 is in operation, the processor 505 is configured to execute instructions stored within the memory 510, to communicate data to and from the memory 510, and to generally control operations of the computer 501 pursuant to the instructions.

The disclosed subject matter can be implemented as a system, a method, and/or a computer program product at any possible technical detail level of integration. The computer program product can include a computer readable storage medium (or media) having computer readable program instructions thereon for causing a processor to carry out embodiments and features of the subject disclosure.

The system can be implemented within a cloud environment. Cloud environments can be provided by a cloud services provider (i.e., "the cloud"). In such cloud environments, data resources can be abstracted among or across one or more computers and/or computer networks that make up the cloud. Examples of cloud computing environments include S3 by Amazon.com.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to exploit features of the present disclosure.

Exemplary Operating Environments

Figure 12:
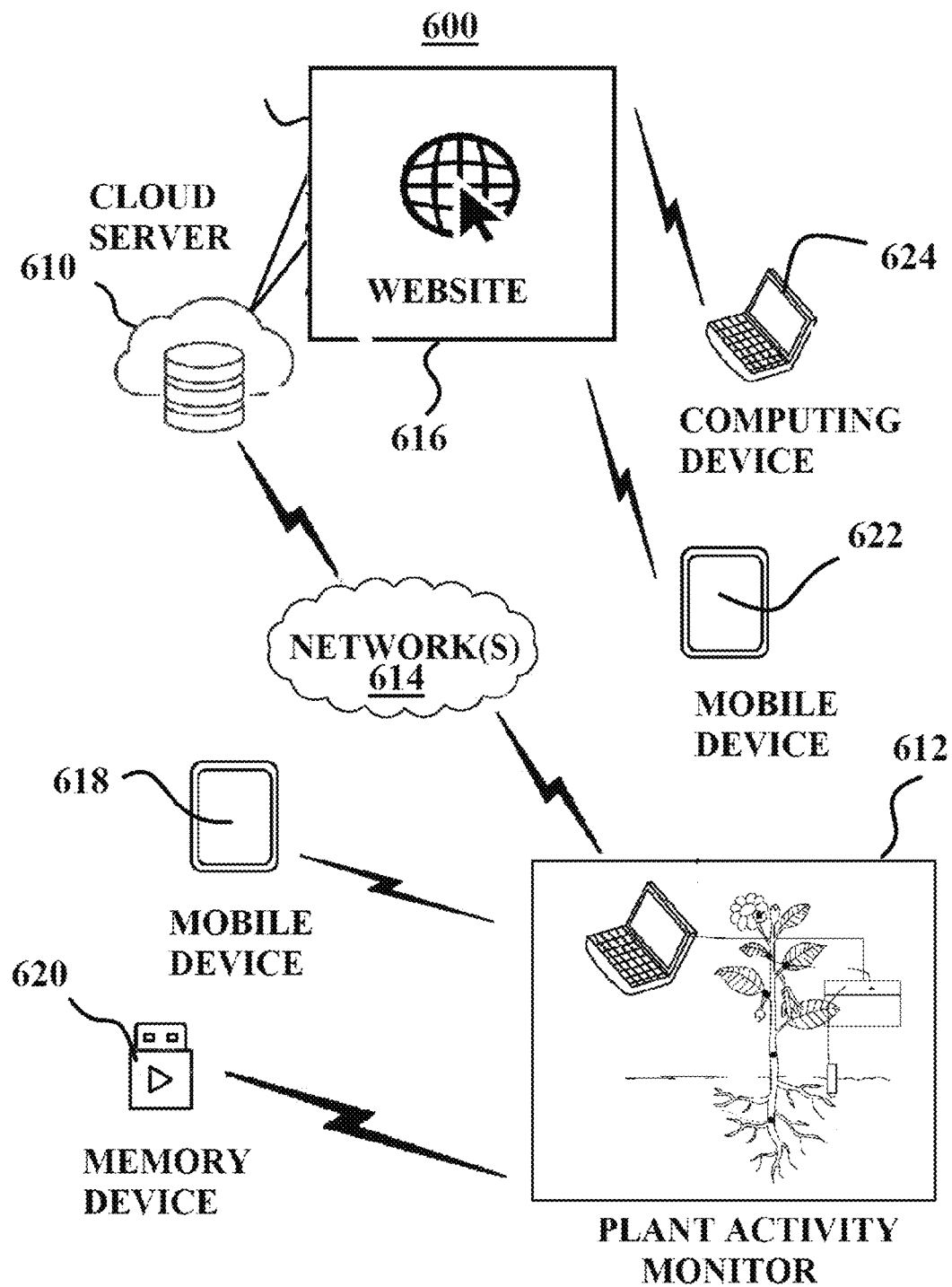
FIG. 12 is a schematic diagram of an exemplary operating environment in accordance with this disclosure.

Referring to FIG. 12 with continuing reference to the foregoing figures, an exemplary operating environment, generally designated by the numeral 600, is shown. The operating environment 600 includes a cloud server 610 that connects to a plant activity monitor 612 over a network 614. The cloud server 610 hosts a website 616. The plant activity monitor 612 can be the system 100 shown in FIG. 1, the system 200 shown in FIG. 2, and/or the system 300 shown in FIG. 3.

The plant activity monitor 612 can be accessed directly by a mobile device 618 and/or by a memory device 620. The website 616 can be accessed by a mobile device 622 and/or a computing device 624. The connections can be wireless or wired connections. In this exemplary embodiment, the connections are wireless.

The plant activity monitor 612 sends data to the cloud server 610 through the network 614. The data can be processed by software on the cloud server 610 to produce output for display on the website 616. The data and/or the output can be stored in data structures or records on the cloud server 610, so that critical data points can be identified.

The output can be displayed on the website 616 to facilitate data analysis and monitoring the health of the plants. Critical health metrics for certain plants have been correlated to potential difference measurements. The operating environment 600 can be utilized to correlate for other plants.

Users can set alarms through the website 616 that can provide an alert when certain health metrics for a plant fall below a critical level. The output can be used to identify certain criteria, such as when a plant is growing, is dying, is sick, and/or needs attention.

Network 614 can be implemented by any type of network or combination of networks including, without limitation: a wide area network (WAN) such as the Internet, a local area network (LAN), a Peer-to-Peer (P2P) network, a telephone network, a private network, a public network, a packet network, a circuit-switched network, a wired network, and/or a wireless network. Computer systems and/or computing devices can communicate via network 614 using various communication protocols (e.g., Internet communication protocols, WAN communication protocols, LAN communications protocols, P2P protocols, telephony protocols, and/or other network communication protocols), various authentication protocols, and/or various data types (web-based data types, audio data types, video data types, image data types, messaging data types, signaling data types, and/or other data types).

The computing devices and/or mobile devices, such as mobile device 618, mobile device 622 and/or computing device 624, can be any type of computing device, including a smartphone, a handheld computer, a mobile device, an edge device, a tablet, a PC, or any other computing device.

The memory device 620 can be any suitable memory device that can be utilized to store plant activity monitor measurements and related data. Suitable devices include Hard Disk Drives (HDD), Solid State Drives, Random Access Memory (RAM), CDs, DVDs, Blu-Ray Discs, DVD-RAM, ROM, and USB Flash Memory.

Figure 13:
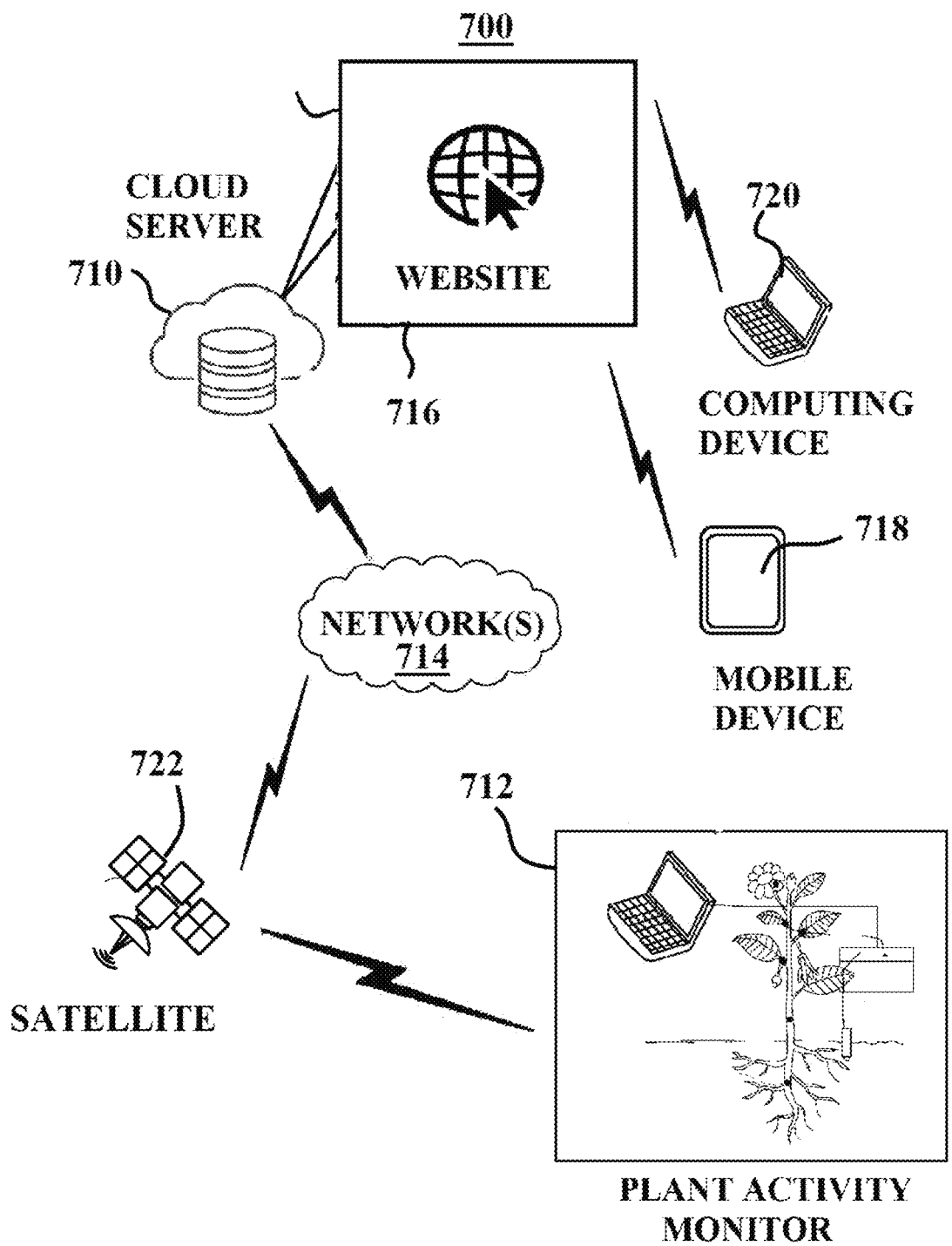
FIG. 13 is a schematic diagram of another exemplary operating environment in accordance with this disclosure.

Referring to FIG. 13 with continuing reference to the foregoing figures, another exemplary operating environment, generally designated by the numeral 700, is shown. Like the embodiment shown in FIG. 12, the operating environment 700 includes a cloud server 710, a plant activity monitor 712, a network 714, a website 716, a mobile device 718, and a computing device 720.

Unlike the embodiment shown in FIG. 12, the plant activity monitor 712 does not connect directly to the network 714 due to the fact that it is placed in a remote location. Rather, the plant activity monitor 712 connects to the network 714 through a communications satellite 722, which can connect to the network 714 to transmit data to from the plant activity monitor 712 to the cloud server 710. The operating environment 700 is particularly suitable for monitoring plants in remote locations.

Supported Features and Embodiments

The detailed description provided above in connection with the appended drawings explicitly describes and supports various features of apparatus and methods for actively or passively monitoring the activity of plants electrochemically. By way of illustration and not limitation, supported embodiments include a system for monitoring the activity of a plant containing an aqueous solution and electrolyte therein, the system comprising: a working electrode for inserting into the plant, a standard electrode for providing a standard electrode, and a data logger for connecting the working electrode to the standard electrode forming an electrochemical cell therebetween, wherein the data logger measures the potential difference between the working electrode and the electrolyte within the plant to provide the ability to compare a measured potential difference of the electrochemical cell with a predetermined critical potential difference for the plant.

Supported embodiments include the foregoing system, wherein the standard electrode is an electrode selected from the group consisting of a reference electrode, a pseudo-reference electrode, solid state electrodes and a quasi-electrode.

Supported embodiments include any of the foregoing systems, wherein the standard electrode is a reference electrode selected from the group consisting of an aqueous reference electrode and a non-aqueous reference electrode.

Supported embodiments include any of the foregoing systems, wherein the standard electrode is a reference electrode selected from the group consisting of a copper-copper (II)sulfate electrode and a silver/silver chloride electrode.

Supported embodiments include any of the foregoing systems, wherein the working electrode includes a corrosion resistant material.

Supported embodiments include any of the foregoing systems, wherein the working electrode includes an oxidation resistant material.

Supported embodiments include any of the foregoing systems, wherein the oxidation resistant material is selected from the group consisting of graphite, stainless steel, corrosion resistant alloys and noble metal alloys.

Supported embodiments include any of the foregoing systems, wherein the noble metals alloys include alloys selected from the group consisting of gold, platinum, silver, palladium, iridium, rhodium, and ruthenium.

Supported embodiments include any of the foregoing systems, wherein the noble metal alloys include metals that have filled electronic d-bands.

Supported embodiments include any of the foregoing systems, further comprising: a computing device for controlling the electrochemical cell, wherein the computing device communicates with the data logger.

Supported embodiments include any of the foregoing systems, wherein data logger determines the potential difference between the working electrode and the reference electrode.

Supported embodiments include any of the foregoing systems, wherein at least one of the data logger and the computing device stores the measured potential difference in memory.

Supported embodiments include any of the foregoing systems, wherein the data logger includes a metering device selected from the group consisting of an ammeter, a voltmeter, a multi-meter, a multi-tester, and an electronic measuring instrument that combines several measurement functions in one unit.

Supported embodiments include any of the foregoing systems, wherein the computing device includes an alarm application for activating an alarm when the difference between the measured potential difference and the predetermined critical potential difference exceeds a predetermined threshold.

Supported embodiments include any of the foregoing systems, wherein the computing device includes an artificial intelligence application for correlating at least one of a predetermined amount of water within the plant, ultraviolet radiation directed toward the plant, nutrient in the plant, and pH level in the soil surrounding the plant to the predetermined critical potential difference for the plant.

Supported embodiments include any of the foregoing systems, wherein the computing device includes an alarm application for activating an alarm when the measured potential difference drops below the threshold for the predetermined critical potential difference for the plant.

Supported embodiments include any of the foregoing systems, wherein the computing device includes an artificial intelligence application for determining the threshold for the predetermined critical potential difference for the plant.

Supported embodiments include any of the foregoing systems, wherein at least one of the computing device and the data logger is coupled to an external network.

Supported embodiments include any of the foregoing systems, wherein the electrochemical cell formed by the working electrode to the standard electrode is a first electrochemical cell, the system further comprising: a second electrochemical cell for injecting electrons into the plant.

Supported embodiments include any of the foregoing systems, wherein the second electrochemical cell includes a pair of electrodes and a power supply connecting the electrodes to one another and wherein the second electrochemical cell drives nutrients from the soil into the plant.

Supported embodiments include any of the foregoing systems, wherein the power supply includes a DC power source.

Supported embodiments include any of the foregoing systems, wherein the DC power source is a solar cell.

Supported embodiments include any of the foregoing systems, wherein the DC power source includes an AC power source and a transformer.

Supported embodiments include a method, a kit, an apparatus, and/or means for implementing any of the foregoing systems or a portion thereof.

Supported embodiments include a method of monitoring the activity of a plant containing an aqueous solution and electrolyte therein, the method comprising: inserting a working electrode into the plant, inserting a standard electrode into at least one of soil surrounding the plant and the plant, connecting the working electrode and the reference electrode to a data logger, and measuring, with the data logger, the potential difference between the working electrode and the standard electrode to provide the ability to compare a measured potential difference with a predetermined critical potential difference for the plant.

Supported embodiment includes the foregoing method, further comprising: activating an alarm when the difference between the measured potential difference and the predetermined critical potential difference exceeds a threshold.

Supported embodiment includes any of the foregoing methods, further comprising: determining the threshold with an artificial intelligence application on the computing device.

Supported embodiment includes any of the foregoing methods, further comprising: coupling the data logger to a computing device.

Supported embodiment includes any of the foregoing methods, further comprising: storing the measured potential difference on at least one of the data logger and the computing device.

Supported embodiment includes any of the foregoing methods, further comprising: correlating, with an artificial intelligence application, at least one of a predetermined amount of water within the plant, ultraviolet radiation directed toward the plant, nutrient in the plant, and PH level in the soil surrounding the plant to the predetermined critical potential difference for the plant.

Supported embodiment includes any of the foregoing methods, further comprising: coupling at least one of the computing device and the data logger to an external network.

Supported embodiment includes any of the foregoing methods, wherein the working electrode and the standard electrode form a first electrochemical cell, the method further comprising: forming a second electrochemical cell with a pair of electrodes consisting of a driving electrode and a counter electrode, and injecting electrons into the plant with the second electrochemical cell.

Supported embodiment includes any of the foregoing methods, further comprising: coupling a power supply to the second electrochemical cell to drive nutrients from the soil surrounding the plant into the plant.

Supported embodiments include a system, a kit, an apparatus, and/or means for implementing any of the foregoing methods or a portion thereof.

Supported embodiments include a kit for monitoring the activity of a plant containing an aqueous solution and electrolyte therein, the system comprising: a working electrode for inserting into the plant, a standard electrode for inserting into at least one of soil surrounding the plant and the plant, and a data logger for connecting the working electrode to the standard electrode to form an electrochemical cell therebetween, wherein the data logger can be configured to measure the potential difference between the working electrode and the electrolyte within the plant to provide the ability to compare a measured potential difference of the electrochemical cell with a predetermined critical potential difference for the plant.

Supported embodiments include the foregoing kit, further comprising: a computing device for implementing an alarm application and an artificial intelligence application.

Supported embodiments include any of the foregoing kits, further comprising: a driving electrode, and a counter electrode, wherein the driving electrode and the counter electrode inject electrons into the plant.

Supported embodiments include any of the foregoing kits, further comprising: a power supply for coupling to the driving electrode and the counter electrode to drive nutrients from the soil to the plant.

Supported embodiments include a system, a method, an apparatus, and/or means for implementing any of the foregoing kits or a portion thereof.

Supported embodiments include a system for collecting data for a plant containing an aqueous solution, ions and electrolyte therein, the system comprising: a plant activity monitor having a working electrode for inserting into the plant, a standard electrode for providing at least one of an electrochemical potential and a predictable voltage, and a data logger for connecting the working electrode to the standard electrode forming an electrochemical monitoring device; a computing device for controlling the electrochemical monitoring device and for communicating with the data logger; and a server connected to a network; wherein the data logger measures the potential difference between the working electrode and the electrolyte within the plant to provide the ability to compare a measured potential difference of the electrochemical cell with a predetermined critical potential difference for the plant; wherein the computing device receives data from data logger and communicates the data to server through the network; and wherein the server stores the data.

Supported embodiments include the foregoing system, wherein the standard electrode is a reference electrode and the data logger determines the potential difference between the working electrode and electrolyte by using the reference electrode.

Supported embodiments include any of the foregoing systems, wherein at least one of the data logger and the computing device stores the measured potential difference in memory.

Supported embodiments include any of the foregoing systems, wherein the data logger includes a metering device selected from the group consisting of an ammeter, a voltmeter, a multi-meter, a digital multi-meter, a multi-tester, and an electronic measuring instrument that combines several measurement functions in one unit.

Supported embodiments include any of the foregoing systems, wherein at least one of the computing device and the server includes an alarm application for activating an alarm when the difference between the measured potential difference and the predetermined critical potential difference exceeds a predetermined threshold.

Supported embodiments include any of the foregoing systems, wherein at least one of the computing device and the server includes an artificial intelligence application for correlating at least one of a predetermined amount of water within the plant, ultraviolet radiation directed toward the plant, nutrient in the plant, and pH level in the soil surrounding the plant to the predetermined critical potential difference for the plant.

Supported embodiments include any of the foregoing systems, wherein at least one of the computing device and the server includes an alarm application for activating an alarm when the measured potential difference drops below the threshold for the predetermined critical potential difference for the plant.

Supported embodiments include any of the foregoing systems, wherein at least one of the computing device and the server includes an artificial intelligence application for determining the threshold for the predetermined critical potential difference for the plant.

Supported embodiments include any of the foregoing systems, wherein at least one of the computing device and the data logger connects to the network.

Supported embodiments include any of the foregoing systems, wherein at least one of the computing device and the data logger connects to the network through a satellite.

Supported embodiments include any of the foregoing systems, further comprising: an electrochemical cell for injecting electrons into the plant.

Supported embodiments include any of the foregoing systems, wherein the electrochemical cell includes a pair of electrodes and a power supply connecting the electrodes to one another and wherein the second electrochemical cell drives nutrients from the soil into the plant.

Supported embodiments include any of the foregoing systems, wherein the server is a cloud server.

Supported embodiments include any of the foregoing systems, wherein the server hosts a website therein.

Supported embodiments include any of the foregoing systems, wherein the server produces output through the website.

Supported embodiments include any of the foregoing systems, wherein the standard electrode is an electrode selected from the group consisting of a reference electrode, a pseudo-reference electrode, solid state electrodes and a quasi-electrode.

Supported embodiments include any of the foregoing systems, wherein the standard electrode is a reference electrode selected from the group consisting of an aqueous reference electrode and a non-aqueous reference electrode.

Supported embodiments include any of the foregoing systems, wherein the standard electrode is a reference electrode selected from the group consisting of a copper-copper (II)sulfate electrode and a silver/silver chloride electrode.

Supported embodiments include any of the foregoing systems, wherein the working electrode includes a corrosion resistant material.

Supported embodiments include any of the foregoing systems, wherein the working electrode includes an oxidation resistant material.

Supported embodiments include a method, a kit, an apparatus, and/or means for implementing any of the foregoing systems or a portion thereof.

Supported embodiments can provide various attendant and/or technical advantages in terms of a simple, economical system and method for monitoring the health and/or activity of a plant. The use of the system and/or methods can be used to increase crop yields.

The system and method can detect changes in soil chemistry, pH, sun exposure, UV radiation exposure, interference/mechanical damage, water, and/or amounts of nutrients that are being absorbed from the surrounding soil, sand, or other growth media.

Supported embodiments include a system or a method that can be used to inject electrons into a plant based upon internal potential difference measures that function as an indicator of plant health.

Supported embodiments include a system or a method that can be used to drive nutrients from the soil into a plant, electrochemically.

Supported embodiments include systems that have applications in drought stress monitoring in which electrodes are inserted into the soil near the roots or into the tree itself to monitor changes in ORP, which can indicate water stress. Such applications help in the early identification of water stress, allowing for timely irrigation or other remedial measures or chemical treatments.

Supported embodiments include systems that have applications in disease detection. In such applications, it has been determined that certain tree diseases can alter the chemical balance within a tree. ORP monitoring can detect these changes, potentially before visible symptoms appear. Such applications provide for early detection of diseases, which can prompt quicker management actions.

Supported embodiments include systems that have applications in nutrient deficiency assessment. In such applications, it has been determined that ORP levels can fluctuate with varying nutrient levels in the soil. Monitoring these changes can indicate nutrient deficiencies to enable better management of fertilizer application and soil health.

Supported embodiments include systems that have applications in environmental pollution monitoring. In such applications, it has been determined that trees absorb various pollutants that can affect their redox status. The monitoring of ORP levels can help in assessing the impact of environmental pollution on tree health.

The detailed description provided above in connection with the appended drawings is intended as a description of examples and is not intended to represent the only forms in which the present examples can be constructed or utilized. It is to be understood that the configurations and/or approaches described herein are exemplary in nature, and that the described embodiments, implementations and/or examples are not to be considered in a limiting sense, because numerous variations are possible.

Although the subject matter has been described in language specific to structural features and/or methodological acts, it is to be understood that the subject matter defined in the appended claims is not necessarily limited to the specific features or acts described above. Rather, the specific features and acts described above are presented as example forms of implementing the claims.

Examples 1-6

Electrochemical potential measurements of an electrochemical cell configured in the same manner shown in FIG.

1 were taken to determine the health conditions of Banyan trees in Hawaii were taken. The measurements correspond to redox potential values trees in which the health conditions range from excellent to dead. These ORP values provide a snapshot of the redox environment, and indirectly measures photosynthetic activity.

Environmental factors, such as soil conditions, water status, and nutrient availability, can affect ORP readings and should be considered when interpreting these values. It provides an excellent tool to see if the agricultural treatment on stressed plant is working The measurements were correlated to observable health indicators, such as color and compactness of the trees, as indicated in Table 1.

TABLE 1

Tree Health Conditions and Redox Potential Measurements

| Tree Species | ORP Value (mV) | Relative Health Rating |
|---|---|---|
| Oak (*Quercus*) | +350 to +450 | Healthy |
| Maple (*Acer*) | +300 to +400 | Healthy |
| Pine (*Pinus*) | +250 to +350 | Moderate |
| Birch (*Betula*) | +200 to +300 | Moderate |
| Cedar (*Cedrus*) | +150 to +250 | Stressed |
| Willow (*Salix*) | +100 to +200 | Stressed |

What is claimed is:

1. A system for collecting data for a plant containing an aqueous solution, ions and electrolyte therein, the system comprising:
   a plant activity monitor having a working electrode for inserting into the plant, a standard electrode, and a data logger for connecting the working electrode to the standard electrode, so that the plant, the working electrode, and the standard electrode form an electrochemical cell; and
   a computing device for controlling the plant activity monitor and for communicating with the data logger with the computing device having memory, a processor, and an alarm application residing in memory;
   wherein the data logger obtains electrochemical potential measurement of the electrochemical cell;
   wherein the data logger sends the electrochemical potential measurement to the computing device;
   wherein the computing device converts the electrochemical potential measurement into an oxidation reduction potential measurement expressed in millivolts using correlations stored in memory;
   wherein computing device sends the oxidation reduction potential measurement to the alarm application; and
   wherein the alarm application sends an alarm when the oxidation reduction potential measurement is below 200 millivolts.

2. The system of claim 1, further comprising:
   a cloud server having a website residing thereon for communicating with the computing device over a network;
   wherein the website displays output indicating that the plant is healthy when the oxidation reduction potential measurement is above 300 millivolts.

3. The system of claim 2, wherein the data logger includes a metering device selected from the group consisting of an ammeter, a voltmeter, a multi-meter, a digital multi-meter, a multi-tester, and an electronic measuring instrument that combines several measurement functions in one unit.

4. The system of claim 3, wherein at least one of the computing device and the data logger connects to the network through a satellite.

5. The system of claim 2, wherein the plant monitor electrochemical cell is a first electrochemical cell within a pair of electrochemical cells with the system further comprising:
   a second electrochemical cell for injecting electrons into the plant.

6. The system of claim 5, wherein the second electrochemical cell includes a pair of electrodes and a power supply connecting the electrodes to one another, wherein the plant is surrounded by soil, and wherein the second electrochemical cell drives nutrients from the soil into the plant.

7. The system of claim 1, wherein the standard electrode is an electrode selected from the group consisting of a reference electrode, a pseudo-reference electrode, solid state electrodes and a quasi-electrode.

8. The system of claim 1, wherein the standard electrode is a reference electrode selected from the group consisting of an aqueous reference electrode and a non-aqueous reference electrode.

9. The system of claim 1, wherein the standard electrode is a reference electrode selected from the group consisting of a copper-copper (II) sulfate electrode and a silver/silver chloride electrode.

10. The system of claim 1, wherein the working electrode includes an oxidation resistant material selected from the group consisting of carbon, noble metals, noble metal alloys, high performance alloys and stainless steel alloys.

11. The system of claim 10, wherein the oxidation resistant material is platinum.

12. The system of claim 1, wherein the data logger includes a metering device selected from the group consisting of an ammeter, a voltmeter, a multi-meter, a digital multi-meter, a multi-tester, and an electronic measuring instrument that combines several measurement functions in one unit.

13. An apparatus for collecting data for a plant containing an aqueous solution, ions and electrolyte therein, the apparatus comprising:
   a plant activity monitor having a working electrode for inserting into the plant, a standard electrode, and a data logger for connecting the working electrode to the standard electrode, so that the plant, the working electrode, and the standard electrode form an electrochemical cell; and
   a computer system for controlling the plant activity monitor and for communicating with the data logger with the computer system having memory, a processor, an alarm application residing in memory and a display device;
   wherein the data logger obtains electrochemical potential measurement of the electrochemical cell;
   wherein the data logger sends the electrochemical potential measurement to the computer system;
   wherein the computer system converts the electrochemical potential measurement into an oxidation reduction potential measurement expressed in millivolts using correlations stored in memory;
   wherein computer system sends output to the display device indicating that the plant is healthy when the oxidation reduction potential measurement is greater than 350 millivolts and the plant is an oak tree or a pine tree;

wherein computer system sends output to the display device indicating that the plant is healthy when the oxidation reduction potential measurement is greater than 300 millivolts and the plant is a maple tree or a birch tree;

wherein computer system sends output to the display device indicating that the plant is stressed when the oxidation reduction potential measurement is less than 250 millivolts and the plant is a pine tree or a cedar tree; and wherein computer system sends output to the display device indicating that the plant is stressed when the oxidation reduction potential measurement is less than 200 millivolts and the plant is a birch tree or a willow tree.

14. The apparatus of claim 13, wherein the computer system includes a cloud server having a website for displaying the output on the display device.

15. The apparatus of claim 13, wherein the data logger includes a metering device selected from the group consisting of an ammeter, a voltmeter, a multi-meter, a digital multi-meter, a multi-tester, and an electronic measuring instrument that combines several measurement functions in one unit.

16. The apparatus of claim 13, wherein the plant monitor electrochemical cell is a first electrochemical cell within a pair of electrochemical cells with the system further comprising:
a second electrochemical cell for injecting electrons into the plant.

17. The apparatus of claim 16, wherein the second electrochemical cell includes a pair of electrodes and a power supply connecting the electrodes to one another, wherein the plant is surrounded by soil, and wherein the second electrochemical cell drives nutrients from the soil into the plant.

18. The apparatus of claim 13, wherein the standard electrode is an electrode selected from the group consisting of a reference electrode, a pseudo-reference electrode, solid state electrodes and a quasi-electrode.

19. The apparatus of claim 13, wherein the standard electrode is a reference electrode selected from the group consisting of an aqueous reference electrode and a non-aqueous reference electrode.

20. The apparatus of claim 13, wherein the data logger includes a metering device selected from the group consisting of an ammeter, a voltmeter, a multi-meter, a digital multi-meter, a multi-tester, and an electronic measuring instrument that combines several measurement functions in one unit.

* * * * *